(12) United States Patent
Pawliszyn et al.

(10) Patent No.: US 9,625,426 B2
(45) Date of Patent: Apr. 18, 2017

(54) STANDARD ANALYTE GENERATOR

(71) Applicants: Janusz Boleslaw Pawliszyn, Waterloo (CA); Jonathan James Grandy, Bridgewater (CA); German Augusto Gomez Rios, Waterloo (CA)

(72) Inventors: Janusz Boleslaw Pawliszyn, Waterloo (CA); Jonathan James Grandy, Bridgewater (CA); German Augusto Gomez Rios, Waterloo (CA)

(73) Assignee: Janusz Pawliszyn, Waterloo, ON (CA)

( * ) Notice: Subject to any disclaimer, the term of this patent is extended or adjusted under 35 U.S.C. 154(b) by 31 days.

(21) Appl. No.: 14/638,544

(22) Filed: Mar. 4, 2015

(65) Prior Publication Data

US 2016/0258910 A1    Sep. 8, 2016

(51) Int. Cl.
| | | |
|---|---|---|
| *B01J 20/281* | (2006.01) | |
| *G01N 1/40* | (2006.01) | |
| *G01N 30/04* | (2006.01) | |
| *B01D 15/10* | (2006.01) | |
| *G01N 30/00* | (2006.01) | |
| *G01N 30/06* | (2006.01) | |
| *G01N 1/28* | (2006.01) | |

(52) U.S. Cl.
CPC ............ *G01N 30/04* (2013.01); *G01N 1/405* (2013.01); *G01N 30/48* (2013.01); *B01L 2300/069* (2013.01); *G01N 2001/2893* (2013.01); *G01N 2030/009* (2013.01); *G01N 2030/045* (2013.01); *G01N 2030/062* (2013.01); *G01N 2030/488* (2013.01)

(58) Field of Classification Search
CPC ............ G01N 1/405; G01N 2030/045; G01N 2030/488; G01N 30/04; G01N 30/48
See application file for complete search history.

(56) References Cited

U.S. PATENT DOCUMENTS

| | | | |
|---|---|---|---|
| 8,278,113 B2 * | 10/2012 | Ermantraut ....... | B01L 3/502707 422/420 |
| 2009/0026122 A1 * | 1/2009 | Pawliszyn .............. | G01N 1/405 210/198.2 |
| 2010/0200491 A1 * | 8/2010 | Dinnean ................ | B01J 20/103 210/315 |

(Continued)

*Primary Examiner* — Jennifer Wecker

(57) ABSTRACT

The invention describes the process by which a standard mixture of organic compounds are spiked and retained onto a composite sorbent matrix for the controlled generation of a standard in fluid above the spiked matrix either in a gaseous or aqueous phase. The novelty of the aforementioned composite matrix stems from the combination of an immobilizing liquid phase such as silicone oil or a polyacrylonitrile solution, and solid, porous particles such as polystyrene-co-divinylbenzene (PS-DVB) or hydrophilic/Lipophilic Balance (HLB) particles to strongly retain the spiked standards. These novel composite mixtures exhibit sorptive capabilities greater than the sum of their individual components. In addition swelling of the particles with the liquid phase facilitates immobilization of the composite sorbent matrix in the vial. With thermodynamic equilibrium strongly favoring the sorbent phase for a wide range of chemical compounds, this invention allows for the reproducible generation of an ultra-low concentration standard analyte mixture in fluid.

10 Claims, 7 Drawing Sheets

(56) References Cited

U.S. PATENT DOCUMENTS

| | | | |
|---|---|---|---|
| 2011/0207637 A1* | 8/2011 | Datta | C08F 210/18 |
| | | | 508/207 |
| 2012/0160038 A1* | 6/2012 | Wells | B01J 15/00 |
| | | | 73/863.21 |
| 2014/0037961 A1* | 2/2014 | Evans | A61K 47/48438 |
| | | | 428/402 |
| 2014/0147925 A1* | 5/2014 | Fuchs | G01N 30/06 |
| | | | 436/92 |

* cited by examiner

STANDARD ANALYTE GENERATOR

FIELD OF THE INVENTION

The presented invention relates to methods of analytical standard preparation where long-term, repeatable loadings of a given standard mixture are needed in GC-based or LC-based applications. The device delivers statistically repeatable amounts of known compounds depending on the initial amount of standard spiked in the sorbent vial and the temperature.

BACKGROUND OF THE INVENTION

Gas chromatography systems, particularly those integrated with mass spectrometry detectors (GC-MS), are undeniably the primary choice in instrumentation for the identification and quantitation of environmentally concerning volatile and semi-volatile organic compounds (VOC's and SVOC's). This prevalence can be confirmed by any modern environmental analysis laboratory where commercial GC-MS instruments have become a mainstay. However, such instrumentation requires meticulous calibration and consistent performance validation to ensure accurate and legally justifiable quantitative results. The calibration process can divided into three separate tasks including: periodic tuning of the instrument, calibration of analyte specific response, and routine quality control (QC) to affirm stable signal.

Classically, GC-MS tuning is performed in two separate stages with both the GC and MS being tuned independently. Contemporary capillary columns in gas chromatography systems are most commonly tuned in terms of linear retention index (LRI) by liquid injection of a wide range of n-alkane species. This process allows end users to normalize the retention time of unknown chemical species to the normal alkane mixture, thus aiding in the identification of these unknown compounds. Regrettably, a given LRI plot is specific to each individual instrument set-up using an explicit GC oven program. This specificity requires that a new LRI plot is generated anytime an instrument component or method parameter is changed requiring a new standard n-alkane mixture to be purchased or prepared.

MS tuning is most commonly performed automatically by direct introduction of a perfluoro-compound vapour into the MS sourced from a liquid calibration vial installed directly on the instrument. Although this process still needs to be performed quite regularly one vial will last for periods exceeding a month.

Following instrument tuning, proper calibration must be performed to adequately relate the arbitrary instrument response to the absolute amount of analyte present in a sample. Regardless of the separation method chosen, (GC or LC) the response of mass spectrometry based detection will vary with chemical structure of a given analyte requiring that different calibration curves, at multiple concentration levels, be prepared for each compound quantified. These curves must also be re-run anytime the signal from the instrument is found to drift as determined by proper QC analyses. With these factors considered it is not surprising that the modern analytical chemist spends more time preparing standard solutions for performing calibration than any other task in the analytical laboratory.

Proper experimental quality control may be considered the final crucial aspect in ensuring legitimate instrument tuning and calibration. QC analyses are intermittently run within a sample-set and the calibration in order to ensure the GC-MS or LC-MS is in-tune and that the detector response remains statistically constant during sample analyses after calibration. In many private and government laboratories some form of QC analysis may be performed as frequently as one in every ten runs. This frequency requires that the amount of analyte loaded from the QC source be as repeatable as possible. Such repeatability can become increasingly difficult in high throughput applications were classically, a single QC solution may be completely exhausted before the instrument signal has shifted requiring an analyst to prepare multiple, QC standards which may introduce unwanted preparative error. This limitation is especially true for volatile standards that cannot be made up in bulk lest analyte is unintentionally lost to the surrounding environment.

It would therefore be advantageous over the prior techniques to implement a calibration technology that could be used multiple times without showing significant depletion. Furthermore it would prove very useful if such a system remains stable over a prolonged period of time, even when highly volatile compounds are present. It is also important that said technology is able to load a quantity of standard that is low enough to be representative of the trace levels of analyte expected from environmental samples. As a final requisite, it should be possible for the device to be manufactured reproducibly at an industrial level. To address these requirements a simple, in-vial standard analyte generator is herein disclosed.

SUMMARY OF THE INVENTION

It is a goal of the present invention to address the multitude of shortcomings presented by classical GC and certain LC based standard preparation wherein commonly used standard mixes may be prepared in a highly reusable and stable standard analyte generating vials. This goal is accomplished by spiking pure standards directly into an immobilizing liquid such as a silicone diffusion pump fluid or a polyacrylonitrile solution which is then mixed with an adsorbent solid particle just as PS-DVB and HLB were chosen in the current invention. The combination of these sorbent phases is shown to present synergistic sorption effects which act to create a portable, highly reusable, automatable, and stable standard analyte generator when placed together in an enclosed container such as a common headspace vial.

Extractions from the presented standard generating vial can be achieved most easily using solid phase microextraction (SPME) devices but may also be performed via direct fluid extraction or with a needle trap device. The array of interface possibilities would allow the invention to be efficiently integrated onto auto sampler sequenced experiments by which multiple, repeatable QC extractions may be performed from a single calibration vial.

Reusable external calibration vial sets may also be prepared by spiking a varying amount of each analyte into separate vials. These stable vials could be re-used any time a calibration curve need be generated on a given instrument, or, used to generate a series of identical calibration curves on multiple instruments in high throughput targeted applications commonly observed in industry.

These, and other uses, characteristics and advantageous of the proposed invention will be most easily understood by those with previous expertise in the field of analytical chemistry. Further understanding by those skilled in the art will be perceptible upon examination of the following drawings, figures and description.

DETAILED DESCRIPTION OF THE INVENTION

The following descriptions will now detail the intricacies of the invention while making reference to the enclosed figures in a manner that shall be comprehensible to those skilled in the art. It is important to note that the subsequent description is meant to be encompassing of the current configuration of the invention and should not be perceived to narrow the claims that follow.

Figure 1:
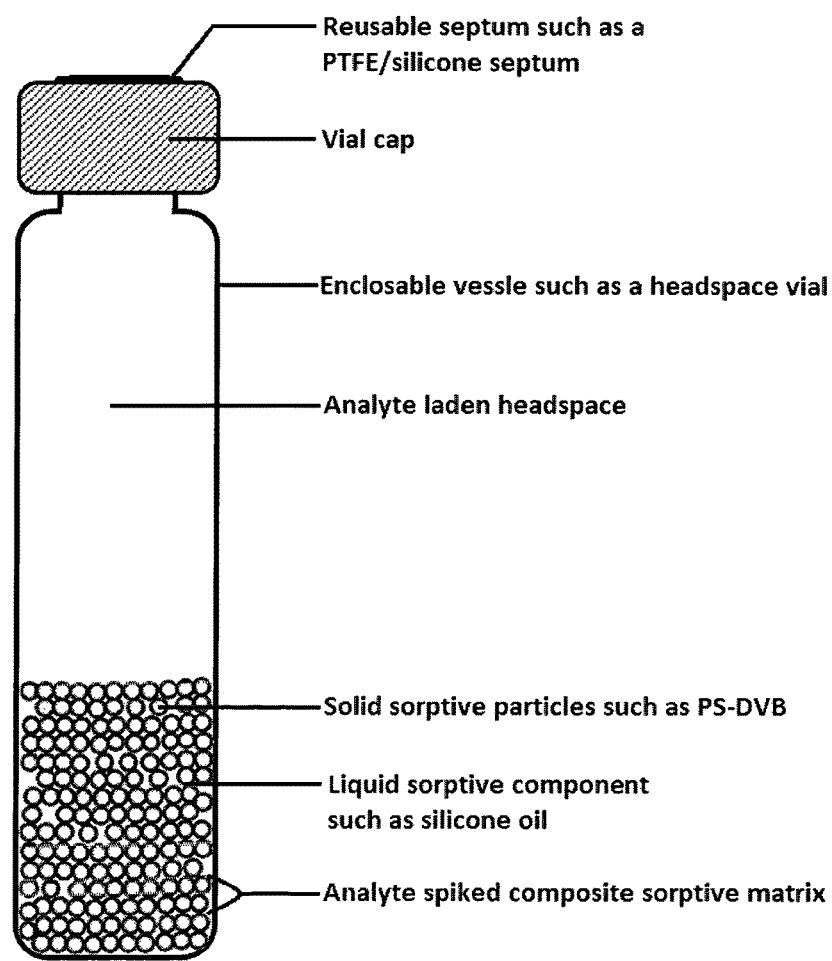
FIG. 1 is provided as a labeled image of the presented invention with a gaseous headspace in a standard configuration for autosampler use, showing a vial with the sorbent matrix, headspace region and standard septum screw cap.

Essentially, the standard analyte generator comprises a capped glass headspace vial (either clear or amber) that has been filled by approximately one-third with a composite sorbent matrix consisting of an immobilizing liquid phase (e.g. silicone diffusion pump fluid or a polyacrylonitrile polymeric solution) and solid sorbent particles (exemplary particles comprised of a polystyrene-co-divinylbenzene (PS-DVB) resin or Hydrophilic/Lipophilic Balance (HLB) particles). This general design is shown in FIG. 1. The sorbent matrix is spiked with standard analytes which are then allowed to come to thermodynamic equilibrium with the static headspace that occupies the remaining two-thirds of the vial volume.

Enclosed in this encapsulating vial, the analytes partition freely between the standard fluid and the composite sorbent matrix. As this process is governed by classical thermodynamic equilibrium, it can be concluded that because compound preference for the sorbent phase is very high, the proportion of analyte available in the fluid remains very small such that the fraction of each compound removed during extraction is statistically negligible resulting in a calibration vial that generates a consistent analyte concentration in the fluid even after hundreds of extractions have been performed. It is worth noting that when very voluminous extractions are performed a small period of time (ca. 5 minutes at 35° C.) is required for a headspace based vial to re-equilibrate. Such a re-equilibration time is well within standard GC run-times which are known to generally exceed 10 minutes.

During sampling of headspace based vials, analytes are extracted from the vial using SPME devices, NTD or direct headspace and then transferred to a GC instrument for analysis. Once re-equilibration of the standard generating vial has occurred, the concentration of the headspace will be statistically similar to how it was before the preceding injection if the temperature was kept constant. It is therefore possible to determine the constant concentration of compound present in the headspace at a given temperature and use the vial for quantitative purposes.

Where the distribution of analyte between the sorbent matrix and the standard fluid is governed by thermodynamic equilibrium it is unsurprising that the concentration of this fluid is highly dependent on the temperature. Proper temperature regulation, as demonstrated by the heater block assembly in FIG. 2, is critical when vials are used for quantitative purposes.

Figure 2:
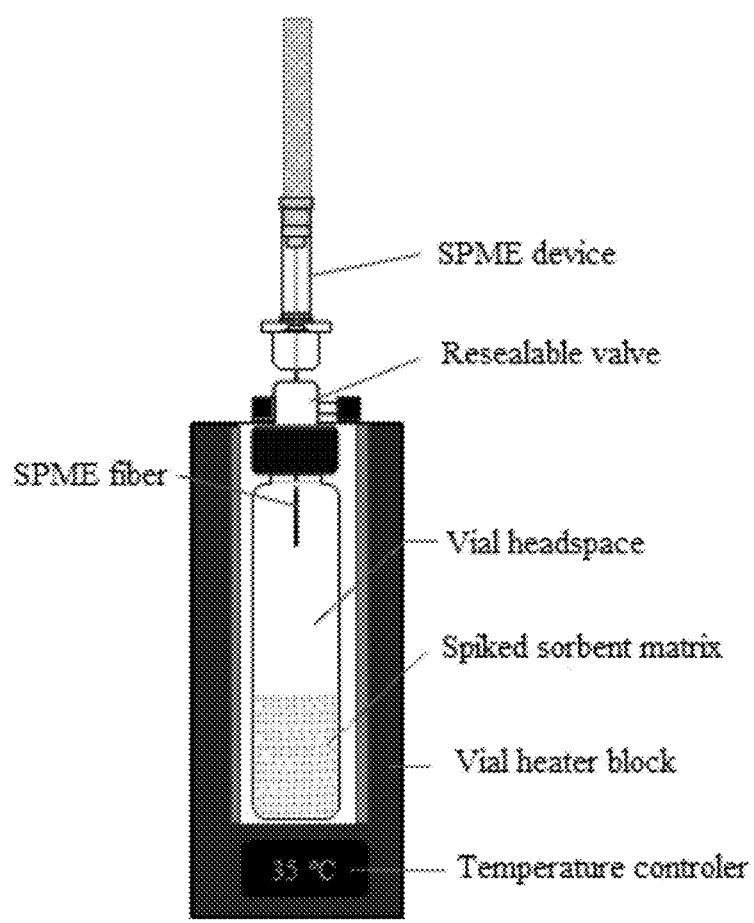
FIG. 2 shows a diagram of the invention with a gaseous headspace in an appropriate configuration for manual use, highlighting the importance of careful temperature control for constant headspace concentrations.
Figure 3:
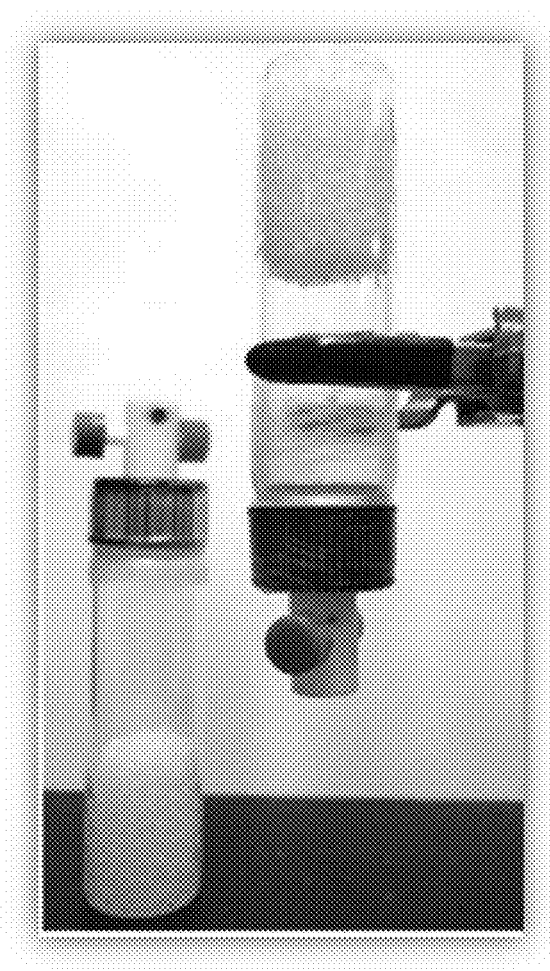
FIG. 3 demonstrates the in-vial adhesion of the PS-DVB particles as a result of swelling from adsorption of the silicone fluid.
Figure 4:
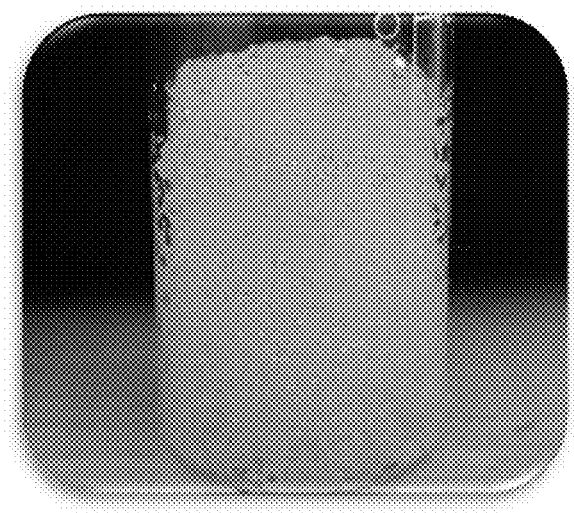
FIG. 4 emphasizes the composite sorbent matrix, highlighting the particle wetting and swelling brought upon by the silicone fluid.

FIG. 1 and FIG. 2 contrast different capping options for the vials. As shown in FIG. 2 a resealable cap such as the commercially available Mininert® valve is the best option if manual extractions are to be performed from the vial as it provides the longest lasting seal. For autosampler implementation the vial may also be capped with a standard 20 mm PTFE/silicone septum placed inside a replaceable screw cap. It is important to note that if the septum is replaced some minor loss of highly volatile analytes from the vial could be observed FIG. 3 and FIG. 4 highlight the additional benefit brought upon by implementing a composite matrix. Once mixed, silicone fluid actively wets and fills the void volume between the particles. The resulting particle swell allows the sorbent matrix to lightly adhere to the vial walls allowing complete inversion of the vial without movement of the PS-DVB particles or silicone oil. Violent shaking of the calibration vial can still result in particles becoming dislodged.

Macroreticular PS-DVB resin, listed under the commercial name as XAD-4® has long been used as a sorbent material for environmental sampling of low molecular weight, (<20 k g mol$^{-1}$) low polarity analytes, however, as with silicone diffusion pump fluid, its' use as a matrix component for reproducible headspace generation is commercially novel to the invention. With this in mind a modified McReynolds test mixture, consisting of benzene, 2-pentanone, 1-nitropropane, pyridine, 1-pentanol, and octane, was chosen to evaluate the headspace based, standard analyte generating vial performance with analytes that represent a variety of inter-molecular interactions. McReynolds mixtures have long been chosen to evaluate stationary phase interactions in GC columns with benzene representing pi-pi type interactions common in aromatics and olefinic compounds, 2-pentanone representing dipole-dipole interactions present in other ketones, aldehydes, and ether groups, 1-nitropropane representing weak proton acceptors such as other nitro and nitrile groups, pyridine representing strong hydrogen bonding and proton accepting effects found in weak basic compounds, 1-pentanol representing compounds with weak proton donating capabilities such as weak acids, alcohol, and chloro groups, and octane representing weak induced dipole-induced dipole interactions such as those found in other alkanes.

To confirm the utility of the current invention, analyte generating vials prepared with the aforementioned six compound McReynolds mixture were prepared and tested for retention capability, depletion rate, long term storage stability, and reproducibility of the manufacturing process.

The materials used in the preparation of the test variant of the current invention were obtained from the following sources. Benzene, 2-pentanone, pyridine, 1-nitropropane, 1-pentanol, and n-octane standards, as well as the PS-DVB particles (Amberlite® XAD-4 and non-branded 5 μm PS-DVB particles), HLB particles (Supel-Select® HLB) high density PLOT PDMS pre-polymer, dicumyl peroxide PDMS catalyst and polyacrylonitrile were purchased from Sigma-Aldrich (Mississauga, ON, Canada). Varian® general purpose mechanical pump oil was supplied by Varian Vacuum Technologies (Lexington, Mass.). KJLC 704 silicone diffusion pump fluid (tetramethyl tetraphenyl trisiloxane) was ordered from Kurt J. Lesker Company (Toronto ON, Canada). 20 mL screw top vials and caps with 20 mm PTFE/silicone septa were purchased from Canada Life Sciences (Peterborough, ON, Canada). 40 mL screw top vials and caps with 22 mm PTFE/silicone septa and 15 mL screw top vials with PTFE Miniert® valves were purchased from Sigma-Aldrich. HPLC grade methanol and dimethylformamide was obtained from Caledon laboratories Ltd. (Georgetown, ON, Canada). Nano-pure water was obtained using a Barnstead/Thermodyne NANO-pure ultrapure water system (Dubuque, Iowa, USA). Drierite desiccant was purchased from W. A. Hammond DRIERITE Co. (Xenia, Ohio, USA). Hamilton brand, 10 μL microsyringes were purchased from Sigma-Aldrich.

Regarding the instrumentation and apparatus used during the evaluation, two separate instruments were employed during the study.

For Experiment 1, an Agilent 6890 GC-5973 quadrupole mass spectrometer was used. Chromatographic separations were performed using a SLBTM-5 MB (30 m×0.25 mm×0.25 μm) fused silica column with a helium flow rate of 1 mL min−1. The column temperature was initially held at 40° C. for 1 min, gradually increased to 50° C. at a rate of 5° C. min−1, then to 70° C. at a rate of 6° C. min−1, and then held for 0.47 min. An injector temperature of 260° C. was used to desorb the DVB/PDMS SPME fiber. During analysis, the transfer line, quadrupole and ion source were set at 280° C., 150° C. and 230° C., respectively. Ionization was achieved using electron impact ionization mode. Full scan mode (40-250 m/z) was used for all compounds, and quantitation was achieved using extracted ion chromatograms.

For Experiments 2, 3, and 4, chromatographic separations and detection, was performed on a Young-Lin Acme 6100 GC-FID using a RTX-WAX (30 m×0.25 mm×0.5 μm) fused silica column with a helium flow rate of 1.3 mL min−1. The column temperature was initially held at 45° C. for 1.5 minutes and then raised to 145° C. at a rate of 12° C. min$^{-1}$, then raised to 180° C. at a rate of 35° C. min$^{-1}$ and held there for 30 seconds. Desorption of the DVB/PDMS and DVB/CAR/PDMS SPME fibers were carried out for 1 minute at a temperature of 260° C. with a split setting of 3:1. Calibration was performed using liquid injection at the same split ratio. The flame ionisation detector (FID) was held at a constant temperature of 300° C. with a fuel mixture consisting of 30 mL min$^{-1}$ of hydrogen, 300 mL min$^{-1}$ of air and 30 mL min$^{-1}$ of helium.

The method used to clean the PS-DVB particles was determined crucial in order to remove major impurities from the resulting vial. Fresh XAD-4 particles were placed into a suitable beaker and manually agitated with an excess of Nano-pure water for 2 minutes, then immediately decanted. This procedure was repeated 3 additional times. Next, the particles were again mixed with Nano-pure water and heated gently to 50° C. for 30 minutes, and then decanted a total of 4 times. The same washing procedure was again repeated, using HPLC-grade methanol instead. Following cleaning, the XAD-4 particles were placed inside a vacuum oven at 60° C. for 24 hours, under nitrogen. The particles were then placed in desiccator units under constant nitrogen purge for at least 48 hours. Failure to properly clean the commercial PS-DVB resin was found to result in heavy contamination of toluene, naphthalene, styrene, various hydrocarbons, and phthalates Preparation and spiking of the silicone diffusion pump fluid was found to be critical in the manufacture of statistically similar headspace based, standard analyte generating vials. Spiked silicone fluid solution was prepared by placing approximately 40 g of oil into 40 mL headspace vials with 0.25 inch stir bars, capped with PTFE/silicone septa. A few microliters of the pure standards were then spiked into the fluid through the septa using a 10 μL microsyringe. This solution was then mixed at 1200 rpm for 48 hours. The exact amount of standard spiked into the oil can be modified to either increase or decrease the headspace concentration of the final product. It was incidentally found that if micro pipetting was used to perform analyte spiking instead, the resulting vials prepared from different batches were not statistically similar.

As the final step in preparation, 1.500+/−0.005 g of the clean XAD-4 particles were accurately weighed into either 20 mL or 15 mL headspace vials to be used with the PTFE septa and Miniert caps, respectively. Then, 3.690+/−0.010 g of the pre-spiked silicone oil was accurately weighed into the vials and immediately capped. These complete standard headspace generating vials were then given at least 48-hours to come to an initial equilibrium. The relative proportions of XAD-4 and silicone fluid remains important to achieve consistent particle swell ratios. In this rendition 2.46 grams of oil were used for every gram of XAD-4, however, for future adaptations a fluid to particle ratio of 2.67:1.00 grams may be preferential.

Figure 5:
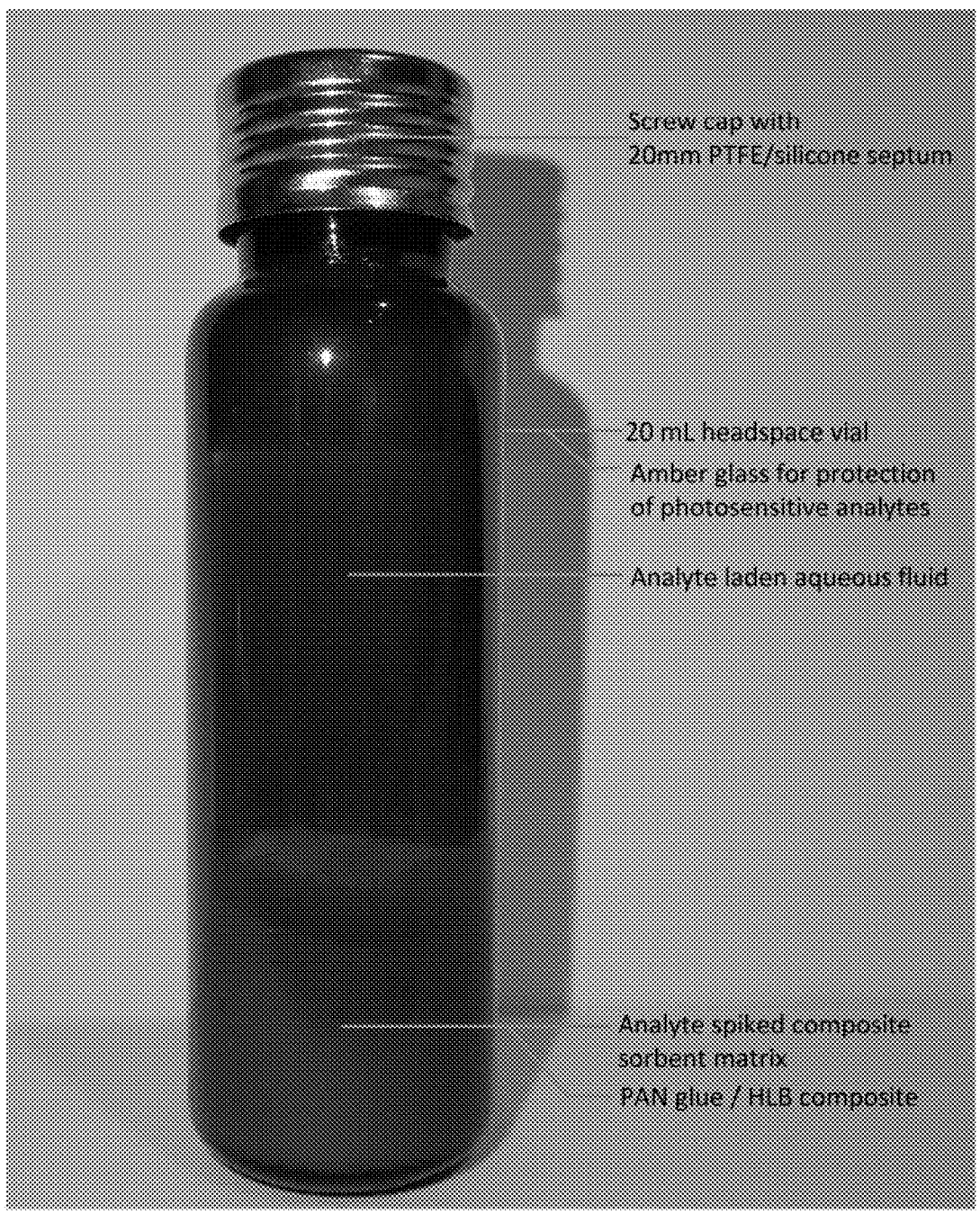
FIG. 5 is provided as a labeled image of the presented invention with an aqueous standard fluid, showing a vial with HLB particles immobilized in the PAN solution polymerized into a gel in the presence of water.

As for the aqueous fluid based standard analyte generator, highlighted in FIG. 5, a composite sorbent matrix consisting of a polyacrylonitrile polymeric solution liquid component mixed with HLB particles was chosen for the vial shown. The example generator shown in FIG. 5 holds the composite sorbent matrix at the bottom of a 20 mL amber glass headspace vial with an aqueous standard media sitting above. This design was further capped with a replaceable 20 mm PTFE/silicone septum screw cap. Such an aqueous fluid based design is preferential for the generation of semi-volatile and non-volatile organic analytes typically analysed by LC-MS instrumentation.

The polyacrylonitrile (PAN), polymeric solution was first prepared by dissolving 4.0 g of polyacrylonitrile granules ($M_w$=150 kDa) into 35 mL of pure dimethylformamide (DMF) in a 40 mL headspace vial. In order to facilitate quicker dissolution the mixture was heated to 90° C. for 1 hour.

As most, non-volatile LC-based analytes occur in the solid state they cannot be spiked into the polymeric solution by use of a syringe. Instead, each analyte was weighed into another 40 mL headspace equipped with a 0.25 inch stir bar by use of an analytical balance. Then, 35 mL of the previously prepared polyacrylonitrile solution was pipetted into this vial which was then capped using a PTFE/melamine cap. The spiked mixture was then mixed at 1200 rpm for 48 hours at a temperature of 90° C. to lower the viscosity of the PAN solution and assist in the dissolution of the solid standard analytes. Again the exact amount of standard to be added will depend on the desired concentration to be generated in the aqueous fluid.

As the final step in preparation, 1.000+/−0.005 g of HLB particles were accurately weighed into 20 mL headspace vials. Then, 4.000+/−0.010 g of the previously spiked PAN solution was accurately weighed into the vials. Because of the inherent viscosity of the PAN solution the mixture was then mixed manually using a spatula, then using a benchtop vortex device for 1 minute, followed by 1 hour of sonication. Finally the remaining vial volume was filled with nano-pure water and capped with a 20 mm PTFE/silicone septum. In addition to serving as the aqueous fluid component of the standard analyte generator, the addition of nano-pure water also causes the polyacrylonitrile solution to partially solidify into a gelatinous matrix effectively immobilizing the HLB particles within it.

The aqueous fluid based standard analyte generator presented in FIG. 5 and paragraphs 39-42 may exhibit relatively long re-equilibration times of the standard analytes in said aqueous fluid after extensive or voluminous extractions have been performed. Said long re-equilibration times stem from the relatively slow distribution kinetics between the sorbent phase and water in combination to the limited interfacial partitioning area available between the aqueous media and composite sorbent matrix. Therefore, a standard analyte generator with vessel walls uniformly coated with a composite sorbent matrix is also presented.

Figure 6:
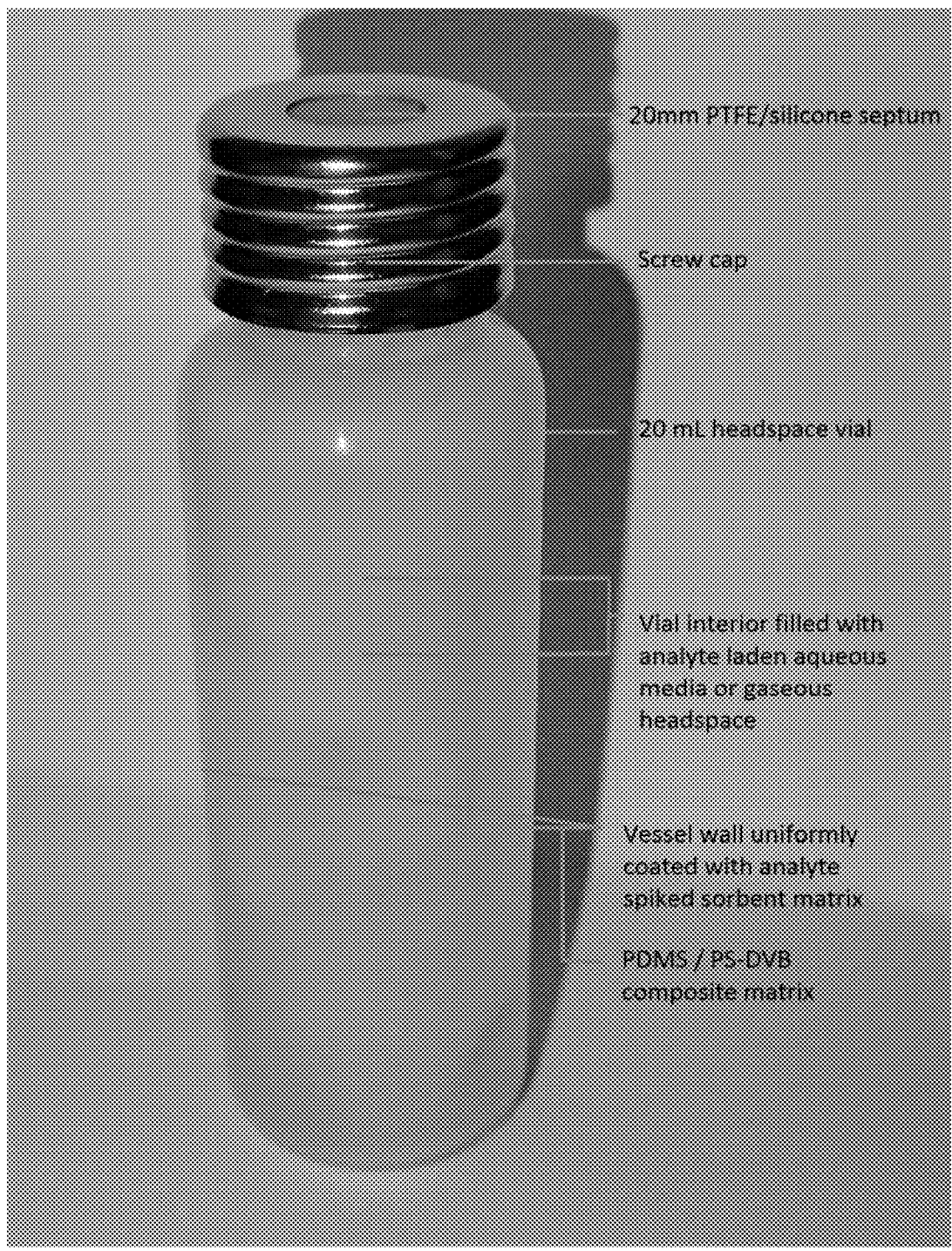
FIG. 6 shows a labeled image of the presented invention with the enclosable vial wall uniformly coated with a composite sorbent matrix consisting of PS-DVB particles immobilized in cross-linked PDMS.

The uniformly coated standard analyte generator as presented in FIG. 6 contains a composite of 5 μm PS-DVB particles immobilized in a cross-linked polydimethylsiloxane (PDMS) liquid component which has been uniformly spread onto the vessel walls of a 20 mL headspace vial capped with a 20 mm PTFE/silicone septum screw cap. The remaining volume of the vial was then filled with nanopure water to act as the aqueous standard media. By employing the entire inner surface area of the enclosable vessel as a region for interfacial partitioning between the composite sorbent matrix and the aqueous fluid much faster standard analyte re-equilibration times will be achievable.

Where PS-DVB particles as small as 5 μm in diameter have a tendency to clump together, 0.120 g+/−0.0010 g of PS-DVB was first suspended in 5 mL of hexane in a 20 mL headspace vial. This mixture was vortexed for 2 minutes followed by 30 minutes of sonication to uniformly suspend the PS-DVB particles in solution. Then, 0.680+/−0.0050 g of PLOT PDMS was added to this solution and vortexed for 2 minutes followed by 1 hour of sonication. Following mixing, nitrogen was lightly bubbled into the solution to drive off most of the remaining hexane as to achieve ideal viscosity for coating of the vessel walls. 20 μL of the dicumyl peroxide catalyst was then spiked into the solution which was then vortexed until the vessel walls were completely coated. Finally, this vial was placed upright in a vacuum oven under nitrogen at a temperature of 220° C. for a period of 16 hours to cross link the PDMS.

Because of the high temperatures required during the cross-linking of the PDMS it was found to be best to spike standard analytes into the vial afterwards. To do this, 100's of milligrams of each analyte were dissolved in 40 mL of an appropriate solvent. 1 mL of this standard solution was spiked into the standard analyte generating vial which was then immediately capped and shaken for a couple of minutes. If the chosen standard analyte mixture is non-volatile, remaining solvent can be evaporated using nitrogen purging. Finally the remaining volume of the vial was filled with nanopure water and allowed to undergo initial equilibration for a period of 24 hours.

Experiment 1

Comparison of the Retention Capabilities of Different Sorbent Matrices

Contrary to what may be initially thought, to maximize vial reusability, it is preferential to have standard analyte generating vial that produces as dilute of a fluid as possible while still producing detectable concentrations when a given amount of analyte has been spiked. As a higher proportion of analyte is retained in the sorbent matrix a lesser fraction remains available for extraction resulting in a vial that depletes much more slowly, remaining reproducible for a greater number of runs.

Figure 7:
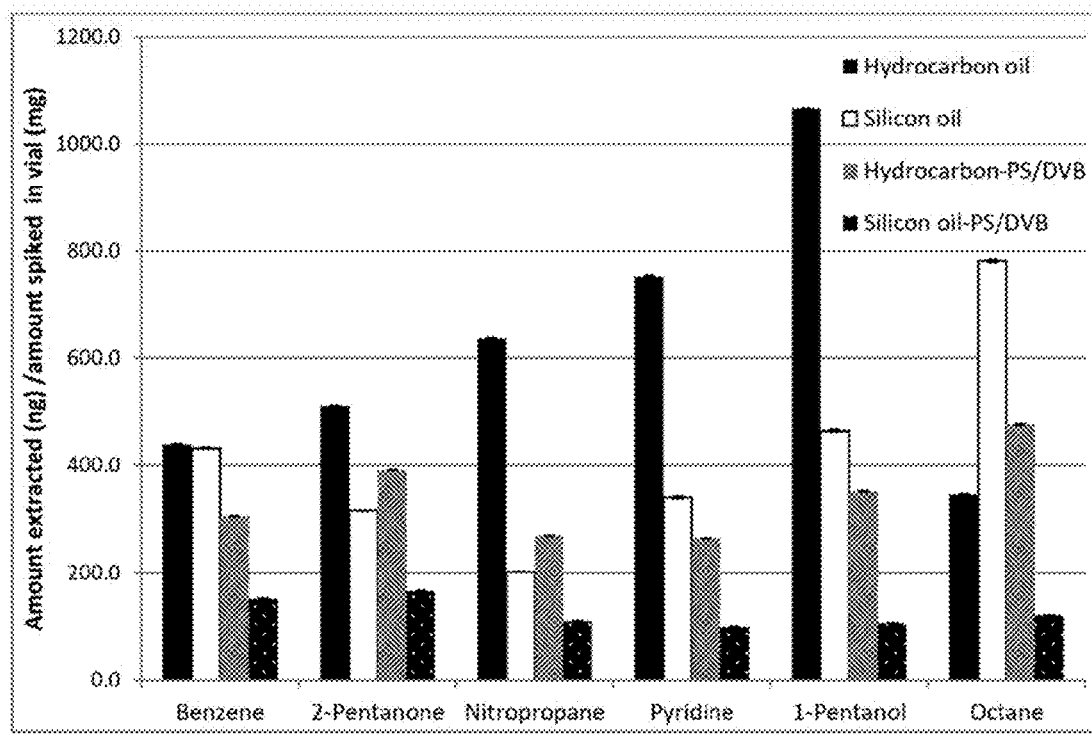
FIG. 7 compares the normalized retention capabilities of 6 different test compounds by standard analyte generating vials prepared using different sorbent matrices including: A. pure hydrocarbon pump oil, B. pure silicone pump fluid, C. a composite mixture of hydrocarbon oil and PS-DVB particles, D. a composite mixture of silicone fluid and PS-DVB particles. Lower extraction amounts represent greater retention by the sorbent and superior standard analyte generating vials. Bars represent the standard deviation of 5 randomized replicate analyses.

Experimentation comparing analyte generating vials prepared using the composite mixture of silicone fluid and PS-DVB particles confirms that this proposed sorbent mixture is at least twice as effective at reducing the amount of all probes extracted from the vial headspace when compared to the former hydrocarbon oil/PS-DVB design (FIG. 7). Interestingly enough, even when pure hydrocarbon oil was shown to be more efficient than pure silicone oil at retaining the lower polarity probes such as octane (Log P value of 4.78) it was still found that the silicone fluid/PS-DVB composite performed better than its' hydrocarbon based counterpart indicating that the silicone fluid/PS-DVB composite mixture exhibits a synergistic retention capability greater than the sum of the individual sorbent contributions. Indeed, it is this finding that demonstrates the major advantage the current invention has over similar, preceding designs discussed in scientific literature.

Experiment 2

Determination and Modeling of the Vial Depletion Rate

Figure 8:
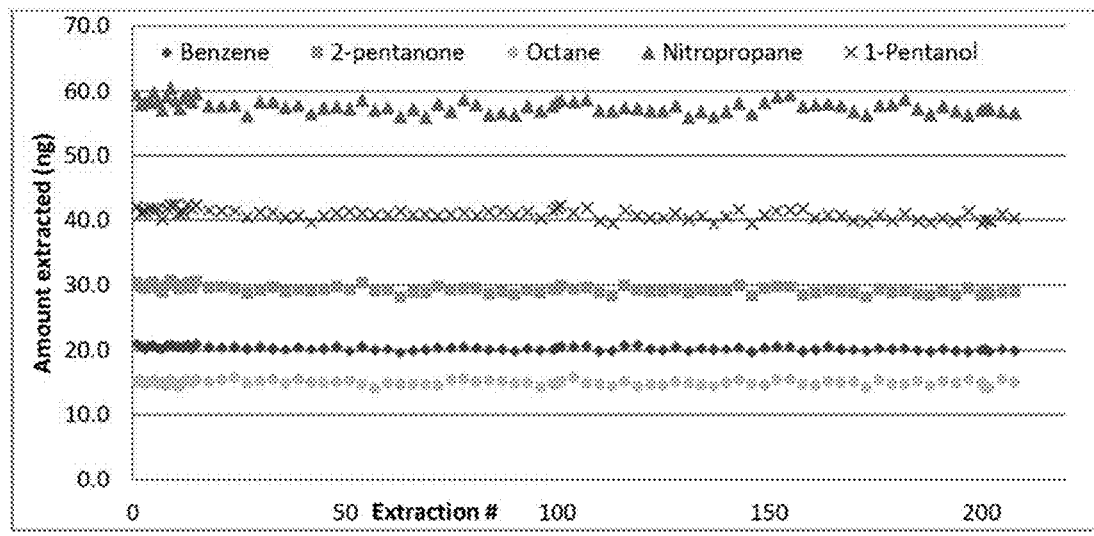
FIG. 8 illustrates the depletion trend for 5 test analytes in a calibration vial prepared with 1.500 grams of PS-DVB and 3.69 grams of silicone fluid after 208 successive, 1-minute headspace extractions were performed using a DVB/CAR/PDMS SPME fiber at 35° C. where only 1 in every 3 extractions were analyzed on a GC-FID.

As alluded to in paragraph 38, the choice of a strongly sorbing retention phase such as the silicone oil/PS-DVB composite should result in a vial that depletes at a negligibly slow rate. This assumption was confirmed experimentally by performing successive, 1 minute extractions from a single standard headspace based, standard generating vial at 35° C. with a high $K_{fs}$ DVB/CAR/PDMS SPME fiber, one of the strongest adsorbing fibers commercially available. (FIG. 8) Even after 208 successive extractions are performed vial depletion is found to be below 3.3% for all evaluated McReynolds probes. (Table 1). Especially considering the sheer quantity of extractions performed, this minuscule depletion should be considered inconsequential for the majority of proposed applications. Hypothetically if such a vial were to be used for experimental quality control, a typical benchtop GC-MS instrument would be expected to experience a shift in signal long before 2000 runs had ever been performed (assuming 1 out of every 10 runs were a QC)

For the odd application that may require an excess of 200 repeatable extractions it is also shown that, if the initial amount of analyte present in the vial is known, depletion can be corrected for by using the presently proposed, theoretical mass fraction based correction equation shown below where $X_{adj}$ is the adjusted amount, $X_n$ is the actual amount extracted at the $n^{th}$ extraction, $\bar{x}$ is the average amount extracted over n runs, n is the number of extractions performed from the vial, and $M_u$ is the initial amount of standard present in the vial. Assuredly, the effectiveness of this correction factor is shown in Table 2 below with a shift in the average amount extracted over the 208 extractions to more closely resemble the initial amount of analyte extracted from the vial when it was new.

$$X_{adj} = X_n + \left((\bar{x}*n)\left(\frac{\bar{x}}{M_o}\right)\right)$$

TABLE 1

Vial depletion of McReynolds probes based on the experimental regression trend and total mass fraction extracted after 208 successive headspace extractions were performed with a DVB/CAR/PDMS SPME fiber at 35° C. for 1 minute.

| Compound | Benzene | 2-Pentanone | 1-Nitropropane | Pyridine | 1-Pentanol | Octane |
|---|---|---|---|---|---|---|
| Experimental depletion trend | | | | | | |
| Initial mass extracted (ng) | 20.5 | 29.7 | 58.1 | 20.6 | 41.5 | 15.1 |
| Final mass extracted (ng) | 20.0 | 28.7 | 56.9 | 20.0 | 40.2 | 14.8 |
| Amount remaining (%) | 97.6 | 96.7 | 97.9 | 97.3 | 97.0 | 98.5 |
| Amount removed (%) | 2.4 | 3.3 | 2.1 | 2.7 | 3.0 | 1.5 |
| RSD of first 15 runs (%) | 1.2 | 1.7 | 1.6 | 1.6 | 1.5 | 2.1 |
| Theoretical (mass fraction) | | | | | | |
| Initial mass per vial (ng) | 178185 | 223713 | 553321 | 225930 | 564826 | 324804 |
| Total mass extracted (ng) | 4257 | 6148 | 12106 | 4272 | 8595 | 3142 |
| Mass remaining in vial (ng) | 173927 | 217564 | 541215 | 221658 | 556231 | 321662 |
| Amount remaining (%) | 97.6 | 97.3 | 97.8 | 98.1 | 98.5 | 99.0 |
| Amount removed (%) | 2.4 | 2.7 | 2.2 | 1.9 | 1.5 | 1.0 |
| Difference between models (%) | 1.1 | −19.0 | 4.4 | −34.5 | −66.4 | −41.7 |

TABLE 2

Comparison of the average amount extracted from a single standard generating vial after 208 successive headspace extractions were performed with a DVB/CAR/PDMS SPME fiber at 35° C. for 1 minute. Comparison is made between the unadjusted data-set, data corrected using the observed experimental depletion, and data corrected using the theoretical mass fraction equation.

| | First 15 extractions (initial) | | | Unadjusted trend | | | Experimental trend adjusted | | | Mass fraction equation adjusted | | |
|---|---|---|---|---|---|---|---|---|---|---|---|---|
| Compounds | Avg | SD | % RSD | Avg | SD | % RSD | Avg | SD | % RSD | Avg | SD | % RSD |
| Benzene | 20.5 | 0.25 | 1.2 | 20.2 | 0.30 | 1.5 | 20.5 | 0.26 | 1.3 | 20.5 | 0.26 | 1.3 |
| 2-Pentanone | 29.7 | 0.51 | 1.7 | 29.2 | 0.57 | 1.9 | 29.7 | 0.47 | 1.6 | 29.6 | 0.47 | 1.6 |
| 1-Nitropropane | 58.1 | 0.94 | 1.6 | 57.6 | 1.0 | 1.7 | 58.1 | 0.91 | 1.6 | 58.1 | 0.92 | 1.6 |
| Pyridine | 20.6 | 0.33 | 1.6 | 20.3 | 0.39 | 1.9 | 20.6 | 0.35 | 1.7 | 20.5 | 0.35 | 1.7 |
| 1-Pentanol | 41.5 | 0.63 | 1.5 | 40.9 | 0.75 | 1.8 | 41.4 | 0.63 | 1.5 | 41.2 | 0.66 | 1.6 |
| Octane | 15.1 | 0.31 | 2.1 | 15.0 | 0.37 | 2.5 | 15.1 | 0.37 | 2.4 | 15.0 | 0.37 | 2.5 |

Experiment 3

Validation of Long Term Storage Stability

Figure 9:
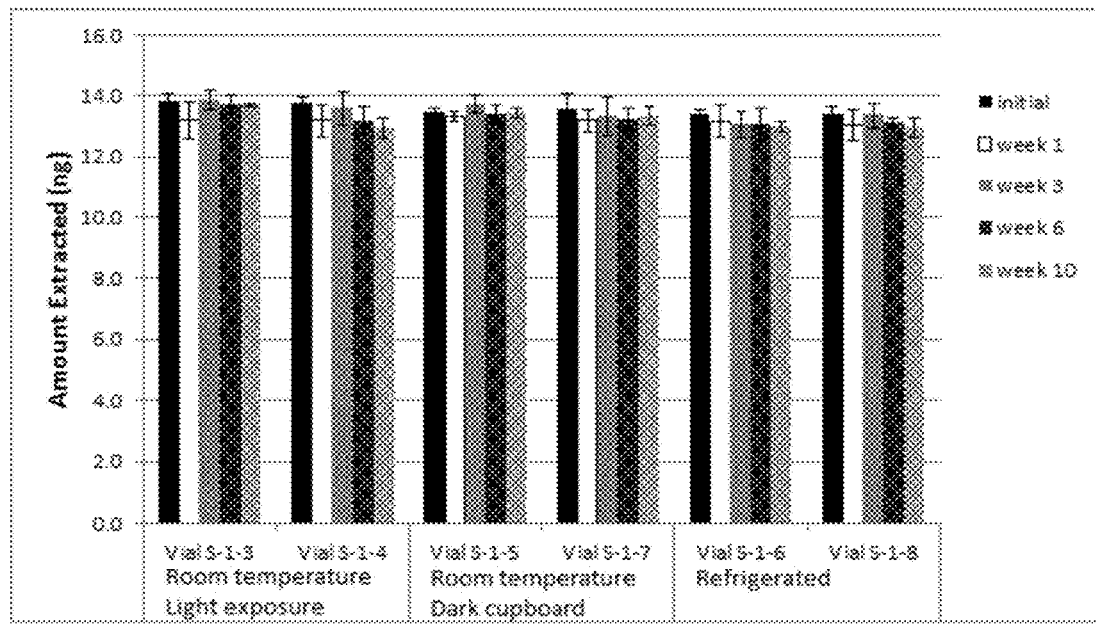
FIG. 9 demonstrates the storage stability of benzene from a calibration vial prepared with 1.500 grams of PS-DVB and 3.69 grams of silicone fluid after vials were stored for 10 weeks under a variety of conditions including: A room temperature with exposure to light, B: room temperature stored in the dark, C: refrigerated in darkness at 5° C. Bars represent the standard deviation of 3 randomized replicate analyses. Extractions were performed at 35° C. with a DVB/PDMS SPME fiber for 1 minute FIG. 10 verifies that calibration vials can be manufactured in a reproducible manner. 6 vials were randomly selected from 3 separate batches of calibration vials that were uniquely prepared using controlled proportions of silicone fluid, PS-DVB, and test analytes. 2 vials from batch 1 (Vial S-1-X), 2 vials from batch 2 (Vial S-2-X) and 2 vials from batch 3 (Vial S-3-X) were tested. Bars represent the standard deviation of 3 randomized replicate analyses. Extractions were performed at 35° C. with a DVB/PDMS fiber for 1 minute.

Another important characteristic of the standard analyte generating vial is the ability to be stored under a wide variety of conditions for extended periods of time. To confirm this finding, 6 different vials were taken and stored under a variety of conditions including 2 vials stored at room temperature with exposure to light, 2 vials stored in a dark cupboard at room temperature and 2 vials stored at 5 in a dark refrigerator. Favourably, it was demonstrated that almost all of the probes tested maintained a statistically constant headspace concentration over the 10 week test period, regardless of the storage condition chosen. (Table 3) To exemplify this finding FIG. 9 clearly demonstrates that benzene, the most volatile probe analyzed, exhibits no-detectable loss regardless of the chosen storage method. The only exception to this finding was found to occur with pyridine in those vials stored with exposure to light. In addition to failing the F-test presented in Table 3, observation of the pyridine data from these 2 vials clearly show a steady, but small decrease in the amount of pyridine extracted over the 10 week period. With that finding it may be advisable to prepare future adaptations of the standard analyte generating vial in amber glass.

It is important to note that vial stability is not limited to the 10 week timeframe chosen for this experiment. It is in-fact, quite possible that the present invention will remain stable for periods exceeding several months.

TABLE 3

ANOVA (95% confidence) confirmation of 10 week storage stability for McReynolds probes spiked in standard analyte generating vials stored at room temperature with light exposure, at room temperature in the dark, and in a dark, 5° C. refrigerator.

| Compounds | Benzene | 2-Pentanone | 1-Nitropropane | Pyridine | 1-Pentanol | Octane |
|---|---|---|---|---|---|---|
| $F_{V1\text{-}3}$ RT, L | 1.40 | 1.53 | 2.53 | 5.38 | 2.20 | 0.02 |
| $F_{V1\text{-}4}$ RT, L | 1.82 | 1.48 | 3.08 | 4.82 | 2.71 | 0.66 |
| $F_{v1\text{-}5}$ RT, D | 1.46 | 3.27 | 2.74 | 3.41 | 2.97 | 0.80 |
| $F_{V1\text{-}7}$ RT, D | 0.28 | 0.30 | 0.52 | 0.34 | 0.78 | *13.89* |
| $F_{V1\text{-}6}$ F, D | 0.57 | 0.22 | 0.53 | 0.20 | 0.09 | 1.53 |
| $F_{V1\text{-}8}$ F, D | 0.91 | 1.29 | 0.87 | 2.07 | 1.46 | 0.35 |
| $F_{crit}$ | | | 3.48 | | | 5.14 |

RT = room temperature,
L = light exposure,
D = storage in dark,
F = storage in fridge 5° C.
*discarded as outlier*

Experiment 4

Validation of Inter-Batch Reproducibility and the Manufacturing Process

Figure 10:
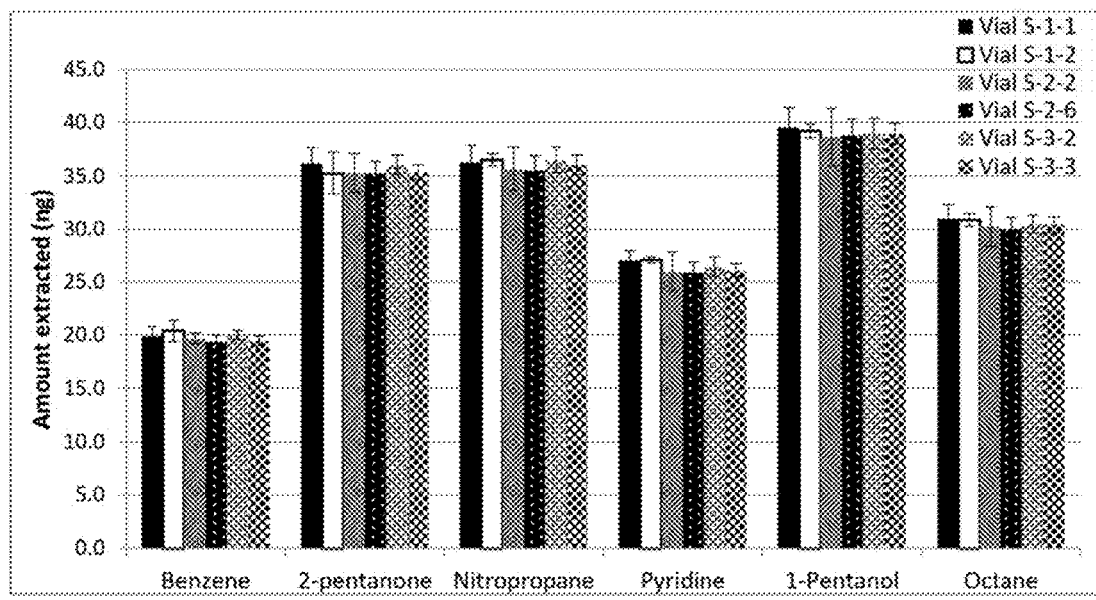

In order to be to be truly appropriate for commercial development it is essential that any quantitative analytical consumable have the capacity to be manufactured in a reproducible manner such that matched sets of standards may be produced. As such, it is demonstrable that standard analyte generating vials produced from multiple unique batches can be made with statistically identical (ANOVA at 95% confidence) headspace concentrations of the McReynolds probes tested if the preparation method described in paragraphs 34, 35 and 36 is strictly followed. (Table 4). This inter-batch agreement can be clearly seen in FIG. 10 with a statistically identical amount of analyte being extracted from every vial.

TABLE 4

ANOVA (95% confidence) confirmation of intra and inter-batch standard analyte generating vial reproducibility with 2 vials selected from each of the 3 prepared batches giving 6 vials total. (n = 3 per vial)

| Compounds | Benzene | 2-Pentanone | 1-Nitropropane | Pyridine | 1-Pentanol | Octane |
|---|---|---|---|---|---|---|
| $F_{vial}$ | 0.85 | 0.28 | 0.30 | 0.72 | 0.11 | 0.29 |
| $F_{crit}$ | | | 3.11 | | | |
| % RSD | 3.4 | 3.5 | 3.3 | 3.8 | 3.7 | 3.4 |
| 2-factor ANOVA test of first factor, inter-vial | | | | | | |
| $F_{vial}$ | | | 1.37 | | | |
| $F_{crit}$ | | | 2.34 | | | |

As it has been demonstrated, standard analyte generating vials prepared using a silicone fluid/PS-DVB composite matrix exhibit all of the pre-requisites defined in paragraphs 8 and 9 for GC based applications. The novel silicone fluid/PS-DVB sorbent matrix has been shown to more strongly retain the test mixture than previous designs resulting in vial that demonstrates negligible depletion following 208 successive, hefty, extractions. Furthermore, the design has also been proven stable for a non-limiting period of 10 weeks under a variety of storage conditions. Lastly, it was clearly demonstrated that the proposed manufacturing method yields gas based vials with statistically identical headspace concentrations even when from completely unique production batches. The aqueous fluid based designs can further be used for the generation of non-volatile standard analyte mixtures which may be very useful for LC-MS based applications. Additionally, further improvement on said design may be accomplished by uniformly coating the entire interior surface of the vessel with an appropriate composite sorptive matrix, especially when quick re-equilibrium of an aqueous fluid is desired. As such the current invention is more than suitable for the preparation of long lasting, multi-use calibration and quality control standards to which there exists a great deal of demand in the analytical chemistry community.

What we claimed is:

1. A device containing standard analytes which are configured to be chemically extracted from a fluid, including by physicochemical interactions, said device consisting of an enclosable vessel containing said fluid configured to be in thermodynamic equilibrium with a composite sorptive matrix characterized by high affinity for said standard analytes in respect to said fluid, said composite sorptive matrix comprising a liquid sorptive component, which is configured to swell a solid sorptive component and facilitate efficient absorption of said standard analytes and immobilize said solid sorptive component onto walls of said vessel.

2. The device as defined in claim 1 wherein said composite sorptive matrix is uniformly dispersed on said vessels walls.

3. The device as defined in claim 1 wherein said fluid is a headspace gas.

4. The device as defined in claim 3 wherein said liquid sorptive component is either a siloxane based fluid or polymeric solution.

5. The device as defined in claim 4 wherein said composite sorptive matrix is PS-DVB particles in silicone oil.

6. The device as defined in claim 4 wherein said composite sorptive matrix is HLB particles in silicone oil.

7. The device as defined in claim 1 wherein said fluid is an aqueous media.

8. The device as defined in claim 7 wherein said liquid sorptive component is a polymeric solution.

9. The device as defined in claim 8 wherein said composite sorptive matrix is HLB particles in polyacrylonitrile solution.

10. The device as defined in claim 8 wherein said composite sorptive matrix is PS-DVB particles in polyacrylonitrile solution.

* * * * *